(12) United States Patent
Heiman et al.

(10) Patent No.: US 7,276,493 B2
(45) Date of Patent: Oct. 2, 2007

(54) FUNGICIDE FOR TREATING PLANTS

(75) Inventors: Daniel F. Heiman, Liberyville, IL (US); Peter D. Petracek, Grayslake, IL (US); Judith A. Fugiel, Lake Villa, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 497 days.

(21) Appl. No.: 10/934,907

(22) Filed: Sep. 2, 2004

(65) Prior Publication Data

US 2005/0059649 A1 Mar. 17, 2005

Related U.S. Application Data

(60) Provisional application No. 60/500,197, filed on Sep. 4, 2003, provisional application No. 60/500,063, filed on Sep. 4, 2003.

(51) Int. Cl.
*A01N 43/34* (2006.01)
(52) U.S. Cl. .................................................... 514/183
(58) Field of Classification Search ................ 514/183
See application file for complete search history.

(56) References Cited

OTHER PUBLICATIONS

Matsushima, Y. et al., "Enantioselective and convergent synthesis of the 20-membered lactam aglycon of vicenistatin antitumor antibiotic," The Journal of Antibiotics, vol. 51(7), 1998, pp. 688-691.*

\* cited by examiner

*Primary Examiner*—John Pak
(74) *Attorney, Agent, or Firm*—Wood, Phillips, Katz, Clark & Mortimer

(57) ABSTRACT

A fungicidal composition and method of treating plant diseases using a compound of formula I.

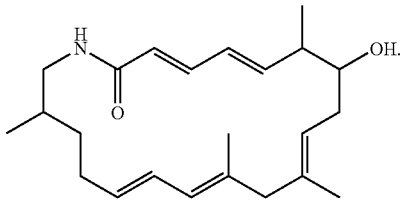

1 Claim, No Drawings

FUNGICIDE FOR TREATING PLANTS

U.S. CROSS REFERENCE TO RELATED APPLICATION

The present application claims the priority of U.S. Application 60/500,197, filed Sep. 4, 2003, which claims benefit of 60/500,063, filed Sep. 4, 2003.

SUMMARY OF THE INVENTION

The present invention is directed to a method of treating various plant diseases comprising applying to the plant locus a fungicidally effective amount of a fungicide of the formula I.

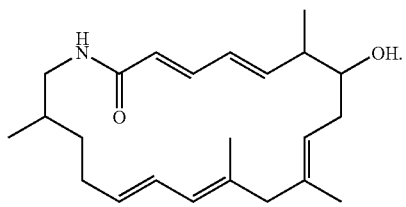

The term "plant locus" means the plant itself, its seed, or the soil surrounding said plant.

The present invention is also directed to a fungicidal composition comprising a compound of formula I and an adjuvant.

DETAILED DESCRIPTION OF THE INVENTION

Compositions of the present invention are comprised of a fungicidally effective amount of the compound described above and one or more adjuvants. The active ingredient may be present in such compositions at levels from 0.01 to 05 percent by weight. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of a finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfocuccinate, sulfated or sulfonated fatty acid esters, petroleum sulfonates, sulfonated vegetable oils, ditertiary acetylenic glycols, polyoxyethylene derivates of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate. Stabilizers may also be used to produce stable emulsions, such as magnesium aluminum silicate and xanthan gum.

Other formulations include dust concentrates comprising from 0.1 to 60% by weight of the active ingredient on a suitable extender, optionally including other adjuvants to improve handling properties, e.g., graphite. These dusts may be diluted for application at concentrations within the range of from 0.1–10% by weight.

Concentrates may also be aqueous emulsions, prepared by stirring a nonaqueous solution of a water-insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. Suitable concentrations of these formulations contain from about 0.1–60% preferably 5–50% weight of active ingredient.

Concentrates may be solutions of active ingredient in suitable solvents together with a surface active ingredient. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water-immiscible ethers, esters, or ketones.

The concentrate compositions herein generally contain from about 1.0 to 95 parts (preferably 5–60 parts) active ingredient, about 0.25 to 50 parts (preferably 1–25 parts) surface active agent and where required about 4 to 94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, performed particles such as preformed and screed particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of this invention may contain form about 0.1 to about 30 parts by weight of active ingredient per 100 parts by weight of clay and 0 to 5 parts by weight of surface active agent per 100 parts by weight of particulate clay.

The method of the present invention may be carried out by mixing the composition comprising the active ingredient into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 10 to 1000 g per hectare, preferably from 50 to 500 g per hectare. The higher application rates will be needed for situations of light soils or greater rainfall or both.

The compounds useful in the present invention may be prepared by methods known to those of ordinary skill in the art.

The fungicide of formula 1 has been evaluated by the following procedures: Contact evaluation.

Compound solution: Contact evaluations were conducted to determine the anti-fungal activity of each compound against *Botrytis cinerea, Sclerotinia sclerotiorum, Pythium aphanidermatum, Rhizoctonia solani, Cercospora arachidicola, Mycosphaerella fijiensis*, and *Monilinia laxa*. Five milligrams of each compound were dissolved in 0.5 milliliter of DMSO for a compound stock solution of 1.0% w/v. Compound stock solutions were serial diluted with DMSO to 20, 10, and 2 ppm final well concentration.

Fungi preparation: *Botrytis cinerea* spores were taken from 6-week-old cultures grown at 22C on full strength potato dextrous agar (PDA) plates. *Sclerotinia sclerotiorum, Pythium aphanidermatum, Rhizoctonia solani*, and *Monilinia laxa* mycelia were taken from 4- to 10-day-old shake flask cultures grown at room temperature on full strength potato dextrous broth (PDB). *Cercospora arachidicola* mycelia were taken from 10- to 14-day-old shake flask cultures grown at room temperature on a full strength PDB amended with peanut oil. *Mycosphaerella fijiensis* mycelia were taken from 10- to 14-day-old shake flask cultures grown at room temperature on V8 juice broth. *Sclerotinia sclerotiorum, Pythium aphanidermatum, Rhizoctonia solani, Cercospora arachidicola*, and *Mycosphaerella fijiensis* mycelia (0.4 g mycelia) were blended for 45 seconds in 20 mL sterile de-ionized water. *Monilinia laxa* mycelia (1 g mycelia) was blended for 45 seconds in 30 mL of sterile de-ionized water. *Botrytis cinerea* spores were diluted with quarter strength PDB to $1 \times 10^5$ spores/mL final well concentration. All mycelia were diluted in water (1:5 mycelia:water) before distributing into the wells.

Microtiter plate preparation: Compound solution (10:L), quarter strength PDB (900:L) and fungi preparation (100:L) were sequentially distributed into 48-well microtiter plates (n=3 replications/compound/rate). A blank consisted of quarter strength PDB and fungi preparation. Commercial fungicide controls (100 ppm diluted with water) consisted of Scala for *Botrytis cinerea*, Dithane F-45 for *Mycosphaerella fijiensis*, and Benlate for *Sclerotinia sclerotiorum, Pythium aphanidermatum, Rhizoctonia solani, Cercospora arachidicola*, and *Monilinia laxa*. Plates were shaken in a circular rotator at room temperature for 20 minutes, then incubated at 25C for 24 to 72 hours, depending on the pathogen.

Fungal control ratings: Fungal growth in wells containing the compounds were compared to the positive control and fungal inhibition was rated as full, partial, or none. Final readings were the average of the three wells (Table 1).

Detached Bean Leaf Bioassay

Compound solution: Compound solutions were prepared by diluting compound stock solutions (1.0% w/v compound in DMSO) to 200 ppm with 0.01% w/v Triton X-100.

Spore solution preparation: *Botrytis cinerea* spores were taken from 6-week-old cultures grown at 22C on full strength potato dextrous agar (PDA) plates and harvested in 1:16 frozen orange juice concentrate:water. *Botrytis cinerea* spore solutions were prepared by diluting spore cultures to $5 \times 10^4$ spores/mL with 1:16 frozen orange juice concentrate:water.

Plant material: Middle trifoliate leaves of greenhouse grown *Phaseolus vulgaris* (Bush bean cv. Blue Lake 274) were excised and placed on a plastic grid above a tray containing moist towels.

Treatment method: One half of the adaxial surface of the leaf was treated with the compound solution (100:L) using a 3 cm Bacti Cell Spreader. A blank consisted of 0.01% w/v Triton X-100. A commercial fungicide control (200 ppm diluted with water) consisted of Scala. After the solutions dried, the trays containing the leaves were covered and held one day in a growth chamber (22C). The adaxial surfaces of the leaves were then inoculated with 5–60:L droplets of *Botrytis cinerea* spore solution.

Fungal control rating: Three days after inoculation with *Botrytis*, the percent necrotic area under the inoculation droplet was determined. Since the areas under the blank (0.01% w/v Triton X-100) were 100% infected, fungal control was expressed as 100 minus the percent necrotic area, and thus 0% infected is 100% fungal control (n=3 leaves/compound, 5 inoculation droplets/leaf, Table 2).

Phytotoxicity ratings: Phytotoxicity was rated as 0=no phytotoxicity, 1=slight phytotoxicity, 2=moderate phytotoxicity, or 3=excessive phytotoxicity (Table 2).

The fungicide of formula I has demonstrated activity as set forth in Tables 1 and 2 below.

TABLE 1

Control of fungi (full, partial, none)

| Organism | Fungiciderate (ppm) | |
|---|---|---|
| Rhizoctinia solani | 20 | Full |
| | 10 | Full |
| | 2 | Full |
| Pythium aphanidermatum | 20 | Full |
| | 10 | Full |
| | 2 | Full |
| Monilinia laxa | 20 | Full |
| | 10 | Full |
| | 2 | Full |
| Botrytis cinerea | 20 | Full |
| | 10 | Full |
| | 2 | Full |
| Cercospora arachidicola | 20 | Full |
| | 10 | Full |
| | 2 | Full |
| Sclerotinia sclerotionum | 20 | Full |
| | 10 | Full |
| | 2 | Full |
| Mycosphaerella fijiensis | 20 | Full |
| | 10 | Full |
| | 2 | Full |

Fungal control of *Rhizoctinia solani, Pythium aphanidermatum, Monilinia laxa, Botrytis cinerea, Cercospora arachidicola. Sclerotinia sclerotionum,* and *Mycosphaerella fijiensis* by compounds in contact evaluations.

TABLE 2

| Botrytis cinerea control (200 ppm) | 31% |
|---|---|
| Phytotoxity (200 ppm) | None |

Fungal control of *Botrytis cinerea* by compounds in a detached bean leaf (*Phaseolus vulgaris*) bioassay and bean leaf phytotoxicity ratings.

The invention claimed is:

1. A method of treating plant diseases comprising applying to a plant locus a fungicidally effective amount of a compound of the formula I

I

* * * * *

UNITED STATES PATENT AND TRADEMARK OFFICE
CERTIFICATE OF CORRECTION

PATENT NO. : 7,276,493 B2  
APPLICATION NO. : 10/934907  
DATED : October 2, 2007  
INVENTOR(S) : Heiman et al.

It is certified that error appears in the above-identified patent and that said Letters Patent is hereby corrected as shown below:

Title page, item [57]

In the Abstract, please delete:

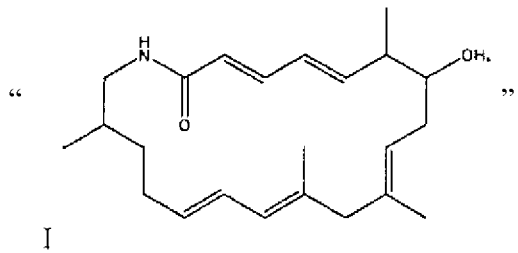

I

And replace it with:

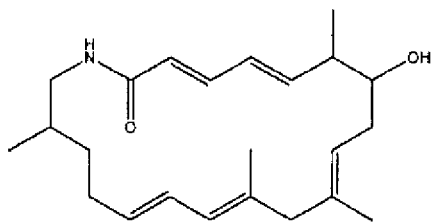

I

UNITED STATES PATENT AND TRADEMARK OFFICE
CERTIFICATE OF CORRECTION

PATENT NO. : 7,276,493 B2
APPLICATION NO. : 10/934907
DATED : October 2, 2007
INVENTOR(S) : Heiman et al.

It is certified that error appears in the above-identified patent and that said Letters Patent is hereby corrected as shown below:

Col. 4, lines 56-64 in claim 1, please delete:

"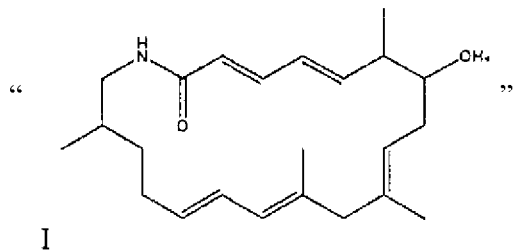"

I

And replace it with:

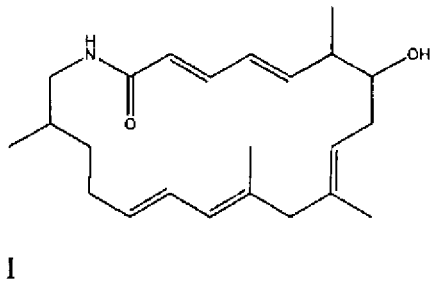

I

Signed and Sealed this

Thirty-first Day of March, 2009

JOHN DOLL
*Acting Director of the United States Patent and Trademark Office*